United States Patent [19]

Misra

[11] Patent Number: 4,673,678
[45] Date of Patent: Jun. 16, 1987

[54] WATER SOLUBLE DERIVATIVES OF FREDERICAMYCIN A

[75] Inventor: Renuka Misra, Frederick, Md.

[73] Assignee: The United States of America as represented by the Secretary of the Department of Health and Human Services, Washington, D.C.

[21] Appl. No.: 889,501

[22] Filed: Jul. 25, 1986

[51] Int. Cl.$^4$ .................. A61K 31/435; C07D 221/18; A01N 43/42
[52] U.S. Cl. ........................................ 514/278; 546/15
[58] Field of Search ........................... 546/15; 514/278

[56] References Cited

U.S. PATENT DOCUMENTS 4,584,377 4/1986 Yokoi et al. ........................... 546/15

OTHER PUBLICATIONS

Pandey et al., (1981) J Antibiotics, vol. 34, No. 11, pp. 1389–1401 "Fredericamycin A, A New Antitumor Antibiotic I."
Warnick–Pickle et al. (1981) J. Antibiotics, vol. 34, No. 11, pp. 1402–1407 "Fredericamycin A, A New Antitumor Antibiotic II."
Hilton et al., (1986) Biochemistry, 25:5533 "Magnetic Resonance Studies of Fredericamycin A".
Byrne et al., (1985) Biochemistry 24:478 "Biosynthesis of Fredericamycin A".
Misra et al., (1982) J. American Chemical Society, 104:4478 "Fredericamycin A, An Antitumor Antibiotic of a Novel Skeletal Type".

Primary Examiner—Robert T. Bond
Attorney, Agent, or Firm—Holman & Stern

[57] ABSTRACT

Water soluble, biologically active derivatives of Fredericamycin A (FMA) and method of synthesizing the same are described. Antibiotic pharmaceutical compositions of the new water soluble compounds of FMA are useful antimicrobial and antitumor preparations.

8 Claims, 5 Drawing Figures

WATER SOLUBLE DERIVATIVES OF FREDERICAMYCIN A

BACKGROUND OF THE INVENTION

1. Technical Field

The present invention is related generally to fredericamycin A. More particularly, the present invention is related to new, water soluble, biologically active derivatives of fredericamycin A and a process for making the same.

2. State of the Art

In 1980 Pandey et al (J. Antibiotics, 34:1389, 1981) reported the isolation and physicochemical properties of a new antitumor antibiotic, fredericamycin A (FCRC-A48, NSC-305263) from a soil isolate of *Streptomyces griseus* (FCRC-48). Based on its ultraviolet-visible spectrum, infra red spectrum, proton and carbon-13 nuclear magnetic resonance spectra and mass spectrum, it was judged to be a novel acid-base indicator type of compound. Among various properties, it was found that fredericamycin A had no activity against Gram-negative bacteria but showed good activity against Gram-positive bacteria and fungi. Furthermore, fredericamycin A was found very cytotoxic. Its $ED_{50}$ against mouse leukemias P388 and L1210 compared closely to the reported values for actinomycin D and adriamycin (Warnick-Pickle et al. J. Antibiotics, 34:1402, 1981).

In vivo studies indicated that fredericamycin A was effective in extending the life span of mice inoculated with P388 leukemic cells and in reducing the median tumor weight of the CD8F mouse mammary tumor. However, it was ineffective against L1210 leukemia, Lewis lung carcinoma, C38 colon tumor, MX-1 breast xenograft, and LX-1 lung xenograft. It showed marginal activity against $B_{16}$ melanoma. Due to poor solubility, further toxicological and pharmacological studies could not be carried out to broaden the utility and range of activity of fredericamycin A.

A number of reports have appeared on the isolation, biological activity, structure and biosynthetic studies of fredericamycin A (Misra et al. J. Am. Chem. Soc. 104:4478, 1982; Byrne et al., 1982 "Biosynthesis of Fredericamycin, A New Antitumor Antibiotic", 22nd Interscience Conference on Antimicrobial Agents and Chemotherapy; Byrne et al., 1985, Biochem. 24:478). However, no mention is made in any of these reports of water soluble derivatives, though a recent publication describes the acetyl, lauroyl and hydrogenated acetyl derivatives (Koichi et al., 1985, Chem. Abst. 103, 104798C, and Koichi et al 1986, Chem. Abstr. 104:33948J). Although these reported derivatives have slightly better solubility in organic solvents, their biological activity is reduced to a great extent compared to fredericamycin A. More importantly, these derivatives are not water soluble which, of course, is an important consideration for preparing formulations and toxicological studies.

SUMMARY OF INVENTION

It is, therefore, an object of the present invention to provide derivatives of fredericamycin A which have water solubility greater than that of fredericamycin A (FMA) and which have equal or better biological activity.

It is another object of the present invention to provide alkali metal salts of FMA, preferred among which are potassium, sodium and lithium salts.

It is a further object of the present invention to provide a method of preparing water-soluble derivatives of fredericamycin A having wide ranging in vitro and in vivo antimicrobial and antitumor activity.

Other objects and advantages of the present invention will become evident as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein.

DETAILED DESCRIPTION OF INVENTION

The above and other objects and advantages of the present invention are achieved by a water soluble compound having the following formula:

wherein at least one of $R_1$, $R_2$ and $R_3$ is an alkali metal moiety, the remaining being either an alkali metal or H.

Unless defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "antibiotic" or "antimicrobial" as used herein means that the compound is effective in preventing or inhibiting the growth of or killing microorganisms and/or tumors when said microorganisms or tumors are contacted with a biocidally effective amount of the compound. The term "biocidal" as used herein means the amount used prevents the growth of or kills only the microorganism or the tumors without harming the host affected with said microorganisms or tumors.

A critical look at the structure and functional groups of fredericamycin A indicates that the molecule inter alia has phenolic hydroxyls and quinone moieties. The phenolic hydroxyl groups are used for derivative purposes. Since these hydroxyls are hydrogen bonded, suitable experimental conditions must be devised so that a water soluble derivative is formed from these phenolic hydroxyl moieties. Hence, various experiments are first performed to determine the optimal conditions for the formation of the water soluble alkali metal salt of fredericamycin A. Having done so, the best mode of preparing the desired compound is now described.

It is important to note here that obtaining a water soluble salt of FMA by simple addition, for example of alkali metal hydroxides, does not yield a detectable derivative. It was discovered that in order to obtain a water soluble alkali metal salt of FMA, certain critical conditions must be met among which are: (a) the reaction must be carried out under deoxygenated conditions; (b) the reaction temperature must be cold, that is 4° C. or less except as noted otherwise; and (c) the alkali metal salt of FMA should be lyophilized and preserved under anhydrous conditions, preferably under $N_2$ and 4° C. or less. The details are now described.

Preparation of the water soluble potassium salt of fredericamycin A

Material and methods:

(A) Apparatus: All glassware is thoroughly cleaned by chromic acid, washed with water, rinsed with a 5% solution of NaOH; again washed with water thoroughly until the water is neutral to Litmus paper and then with distilled deionized water, MeOH, acetone and finally dried.

(B) Reagents and Solvents:

All reagents and solvents used are of analytical reagent quality and obtained commercially.

Any basic solvent which solublilizes FMA can be used. Preferred, however, are solvents such as pyridine or any derivative thereof, piperidine, di- or tri- methyl or ethyl amine, dimethyl formamide, dimethyl acetamide and the like. The most preferred is pyridine.

Pyridine (99+%; spectral grade; Gold label, Aldrich Chemical Company) is freshly distilled (bp 114.5° C.) from KOH pellets.

Any alkali metal hydroxide (low in chloride, and carbonate "Baker" analysed reagent) can be used. Hydroxide solution is made using deionized water from a Milli Q system. Preferred alkali metal hydroxides are KOH, NaOH and LiOH.

All solvents are thoroughly degassed by bubbling dry nitrogen through the solution for several hours prior to use.

The starting compound, fredericamycin A, used in the preparation is greater than 97% pure.

Determination of Antimicrobial and Antitumor Activity:

Protocol for determining in vitro antitumor activity

The assay used for determining in vitro cytotoxic activity of alkali metal salt of FMA is known as "Microculture Tetrazolium Assay" (MTA) developed by the in vitro Cancer Pharmacology R & D Laboratory at NCI-FCRF. The method utilized is a modification of Procedure by T. Mosmann et al., (J. Immunol. Meth. 65:55, 1983 and 70:257, 1984) described by M. C. Alley et al (Proc. AACR. 27:389, 1986). The testing of alkali metal salt of FMA is done using P388 acites murine leukemia as the test system at a inoculation density of about 1000 cells per well and culture duration of 5 days, with various concentration levels of alkali metal salt of FMA vs fredericamycin A. The concentration range could be from 0.1 μg to 10 μg per ml. The results are recorded as percent of control O.D. for each sample dilution.

Protocol for determining in vivo antitumor activity

The antitumor activity is determined by contracted accessary testing services according to the National Cancer Institute (NCI) guidelines for natural products (Geran et al. protocols for Screening Chemical Agents and Natural Products Against Animal Tumors and other Biological Systems. *Cancer Chemother. Rep.* part 3, 3:7–61, 1972; Schepartz: Antitumor Screening Procedures of the National Cancer Institute. *Japan J. Antibiotics* 30 (Supl): 35–40, 1977.)

Alkali metal salt of FMA is tested in vivo against P338 leukemia. The test is carried out using male CD2F1 mice (wt.=18 g±3 g) in one experiment and female mice (wt, 17 g±3.0 gm) in another experiment. Solutions of alkali metal salt of FMA are prepared fresh daily using water as a vehicle and administered intraperitonially at a concentration selected for testing.

Protocol for determining antimicrobial activity against *Bacillus subtilis* and *Penicillium notatum*

These were performed by Disc method, using standard assay procedures and the respective microorganism in each case. 15 μl of each sample in DMSO-H $H_2O$ (1:1) is pipetted on to separate 0.25" absorbent paper disc and the assay is performed following routine techniques well known in the art. Zone sizes are read after incubation overnight (*Bacillus subtilis*) and after 4 days of incubation (*Penicillium notatum*) at various concentrations.

EXAMPLE 1

As an illustrative example, preparation of K-FMA (NSC #601617) is now described.

In a 100 ml round bottom flask provided with a glass stopper and magnetic stirrer is placed fredericamycin A (51.7 mgs; 0.0959 mmols). Pyridine (5.0 ml, freshly distilled from KOH or distilled and kept over KOH overnight, degassed completely for 1 hour using $N_2$) is added to the flask. This mixture is first shaken by hand and then magnetically stirred for 5 minutes at room temperature. It is essential that the solution is homogeneous and transparent. Nitrogen is bubbled through the clear purplish red solution immediately. An aliquot (20 μl) at zero time is taken for UV-VIS analysis. The solution is cooled in an ice bath at about 0° C. for about 50 minutes with stirring. Before adding the KOH solution, the solution is checked again for homogeneity. To this 0°–5° C. solution of fredericamycin A in pyridine, under a nitrogen atmosphere, is added in one lot the KOH solution in 1:3 mols [26.64 mls (0.2781 mmols); 0.0108N, precooled in an ice bath to 0° C. prior to adding for half an hour and degassed]. The flask is swirled by hand at 10° C. for 5 minutes and then stirred magnetically for 4 minutes at 0° C. The solution immediately changes to a bluish green color, and is homogeneous. Samples (30 μl and 40 μl) are taken for UV-VIS, and hydrolysis (HPLC, TLC) respectively at 0 hr. Nitrogen is bubbled through the solution; pH of this solution is about 9.54. It is then stirred for about 30 min at 0° C., the dark blue color deepens and the pH is about 9.43 (5° C.). The solution is checked by UV-VIS, HPLC and TLC as above at half hour. Nitrogen atmosphere is maintained and the solution is stirred magnetically for another 10 minutes at 0° C. A final sample for UV-VIS, HPLC and TLC is taken, pH is about 9.30. (Total time of stirring at 0° C. is about 44 minutes and at 10° C. about 16 minutes. Total reaction time is about 1 hour). The dark blue-green homogeneous solution is frozen (dry ice-acetone, −78° C.) and lyophilized until the compound is completely dry (48 hours). The blue-green solid is transferred into an amber colored container under nitrogen atmosphere and anhydrous conditions, sealed tightly and stored at 0° C. over silica gel. The compound is stable for several months under such conditions. The yield is about 61.6 mgs (98.4%). Thin layer chromatography (TLC) shows a single spot [acid hydrolysed product of salt: plates precoated E. Merck, silica gel-60 F254, 5×20 cm×0.25 mm; solvent system: $CHCl_3$-MeOH-AcOH (87:3:3)] and the high performance liquid chromatography (HPLC) [acid hydrolysed product of salt: column $C_{18}$ μ-bondapak-CN (3.9×15 cm×10 micron); solvent system: $CH_3CH$-$H_2O$-AcOH 40:60:1; flow rate: 1.0 ml/minute; chart speed: 0.5 cms/minute; detection: UV 254 nm; AUFS 0.1] gives a single peak with a retention time of about 6.5 min.

From the potassium salt, the fredericamycin A can be recovered after acid hydrolysis in 99% yield (Quantitative HPLC) and was similar in all respects with the authentic fredericamycin A standard, thus indicating the true nature of the potassium salt derivative.

The potassium salt of fredericamycin A (NSC #601617) is soluble in water with hand shaking for 1 minute, followed by vortexing for 3 minutes. The solubility is about 1.0 mg/ml and gives a transparent blue solution, pH 8.65 with no residue upon membrane filtration (0.22μ, HA, Millipore Products). This solution is stable for almost an hour at room temperature. The anhydrous salt, of course is stable for extended period of time at room temperature.

EXAMPLE 2

Preparation of Na-FMA

Fredericamycin A (15 mg, 0.0278 mmols) is treated with NaOH solution, 1:3 mols (7.65 mls; 0.0109N, degased previously and cooled to 0° C.) in pyridine solution at 0° C. (2.5 ml, degased) under $N_2$ atmosphere. Reaction is carried out by stirring magnetically for 60 minutes under $N_2$ atmosphere. (40 minutes at 0° C. and 20 minutes at 15° C.). The progress of reaction is followed by TLC, HPLC (of hydrolysed product of the Rx mixture) and UV. The resultant blue-green clear reaction mixture is frozen (−70° C.) and lyophilized (48 hrs) until a solid is obtained. Solid is dried (high vacuum at 60° C. for 4 hrs) to yield amorphous highly hygroscopic dull blue-green sodium salt of fredericamycin A, yield 98%. It is soluble in water (0.5 mg/ml) with hand shake and sonication (15 minutes). The solution is stable at room temperature for about ½ hr–1.0 hr, hydrolyzing back to fredericamycin A on longer standing. pH (water) 9.2±0.5. TLC and HPLC (after hydrolysis) show single spot and single peak respectively showing that the product is pure. Its UV, IR, $^1$HNMR is similar to potassium salt of fredericamycin A, FABMS showed M+ as m/z 562 and 584 for mono and disodium salt of FMA.

EXAMPLE 3

Other Alkali-metal salts of FMA

Other alkali-metal salts of FMA are synthesized in the same manner as described for K-FMA in example 1.

Characterization of Potassium Salt of fredericamycin A:

Physicochemical properties of K-FMA are listed in Table 1.

The first indication of the salt formation is observed by solubility studies in water. The isolated potassium salt is more soluble in water (about 1.00 mg/ml) as compared to fredericamycin A which is almost insoluble in water under similar conditions.

Figure 1:
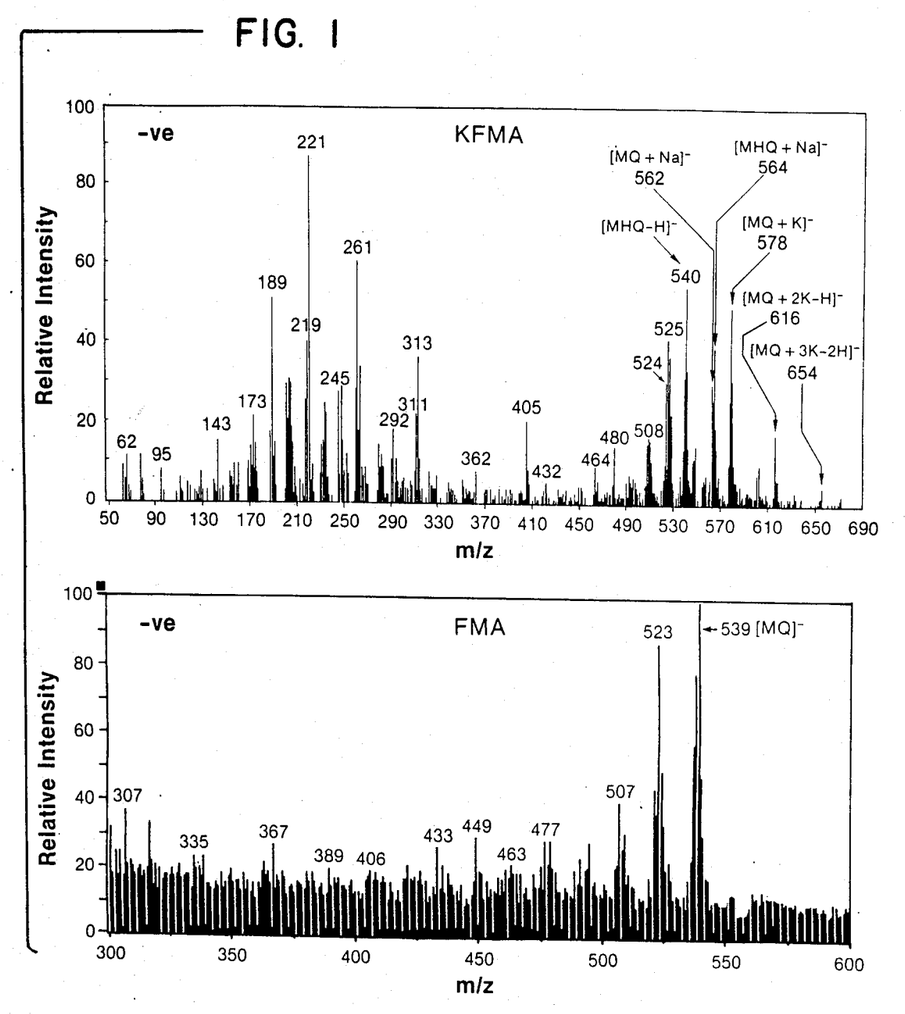
FIG. 1 shows a comparison of fast atom bombardment mass spectra of potassium salt of fredericamycin A (KFMA) with fredericamycin A in negative ion mode using glycerol- DMF(1:1).

Fast atom bombardment mass spectrum (FABMS) in negative ion mode (FIG. 1) clearly indicates the presence of tri-potassium $[MQ+3K-2H]^-$ with an ion at m/z 654, the di-potassium salt with an ion at m/z 616 $[MQ+2K-H]^-$ and mono-potassium salt of FMA with ions at m/z 580 $[MHQ+K]^-$, 579 $[MHQ+K-H]^-$, 578 $[MQ+K]^-$, 577 $[MQ+K-H]^-$, 576 $[MQ+K-2H]^-$). Some ions due to the mono-sodium salt of fredericamycin A (m/z at 564 $[MHQ+Na]^-$, 563 $[MHQ+Na-H]^-$, 562 $[MQ+Na]^{-1}$) are also present in the spectrum. Table 2 shows assignments of ions in the negative ion mode in FABMS.

Figure 2:
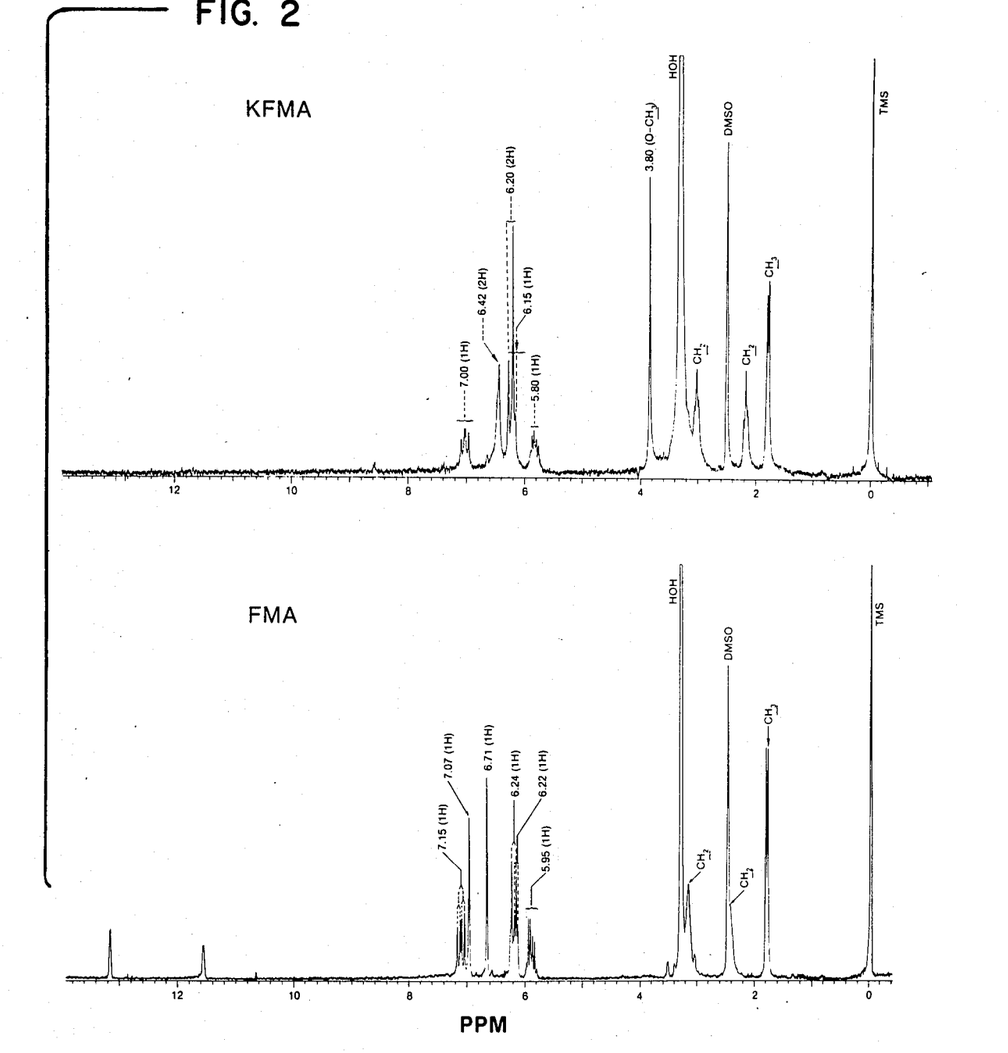
FIG. 2 shows a comparison of proton magnetic resonance (PMR) spectra of potassium salt of fredericamycin A (top) and fredericamycin A (bottom) in DMSO-$d_6$.

The proton magnetic resonance ($^1$HNMR) spectrum of the potassium salt in DMSO-$d_6$ clearly shows all the proton signals, not otherwise observed in the spectrum of fredericamycin A. A comparison of the two spectra is shown in FIG. 2 and Tables 3 and 4.

Figure 3:
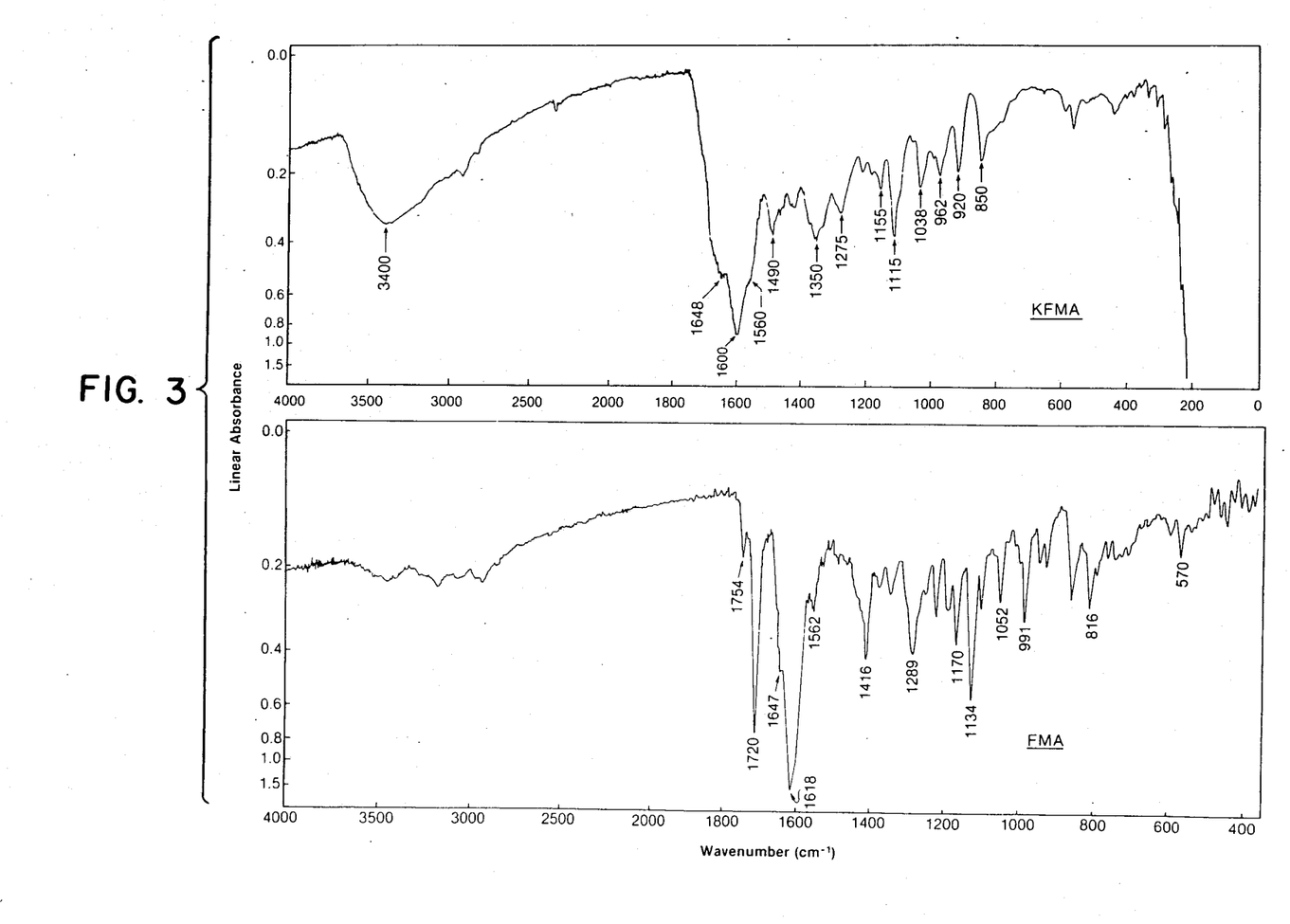
FIG. 3 shows a comparison of infrared spectra of potassium salt of fredericamycin A (top) and fredericamycin A (bottom) in KBr pellet.
Figure 4:
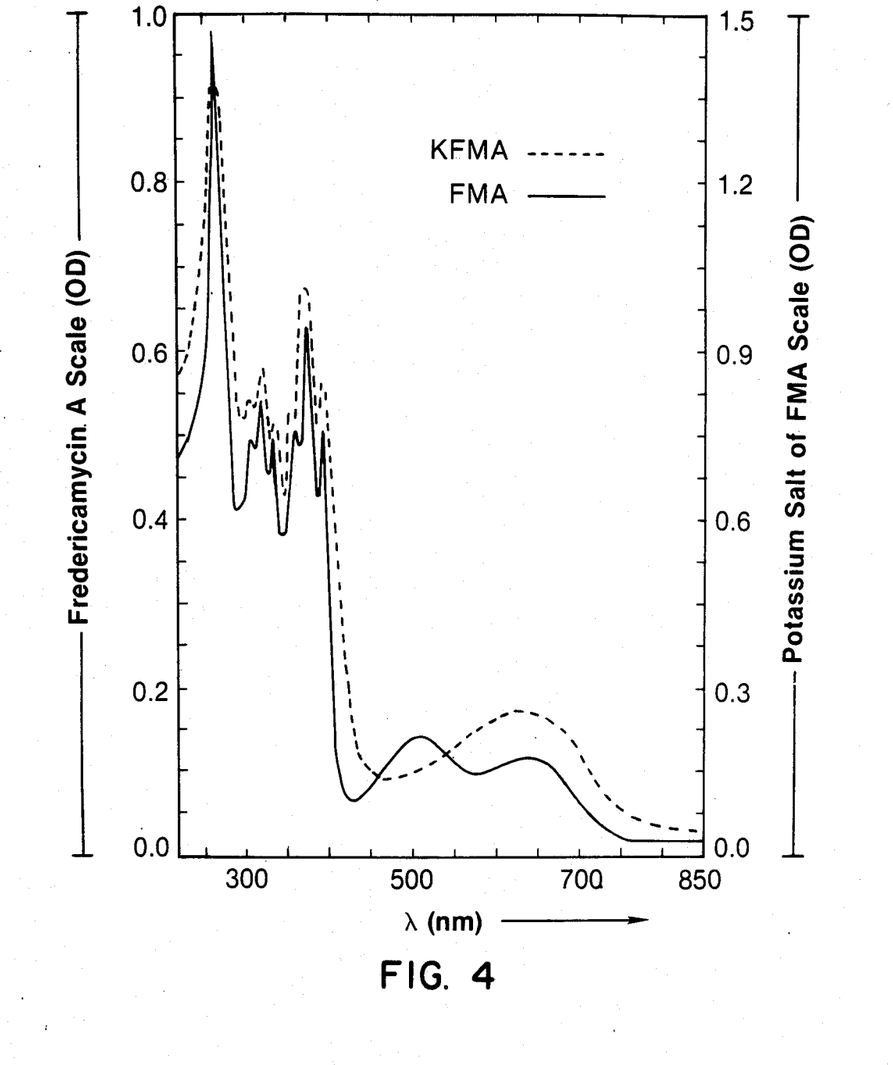
FIG. 4 shows a comparison of UV-Visible spectra of KFMA (—) and FMA (—) in DMF-MeOH (2:8)

An infra red comparison of the potassium salt of fredericamycin A and fredericamycin A is shown in FIG. 3. Comparative UV-VIS spectra are shown in FIG. 4 and Table 5.

A comparison of in vivo biological activity of fredericamycin A and the potassium salt of fredericamycin A is shown in Table 6. The data indicate that KFMA shows significant activity in all experiments performed against P388 leukemia cell line with T/C value of 178% at 1 mg/kg level. There were no differences observed between male and female mice.

Figure 5:
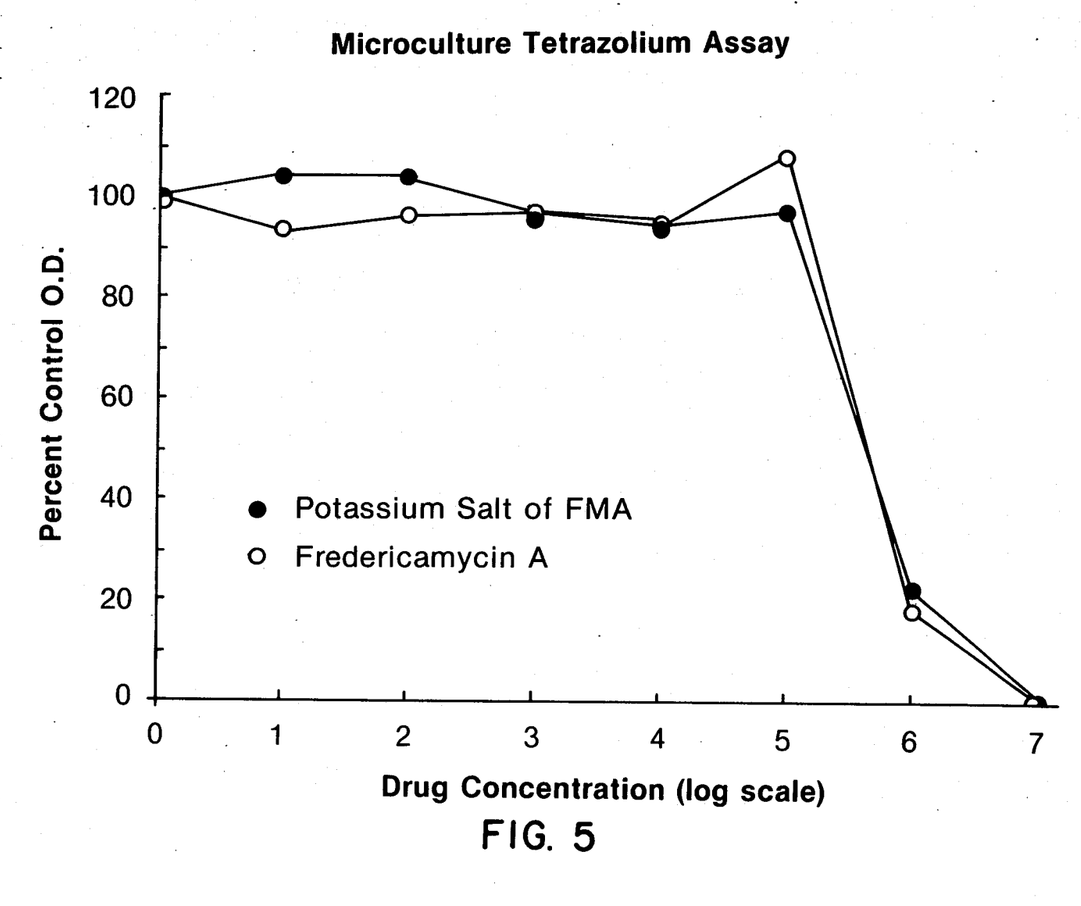
FIG. 5 shows a comparison of in vitro cytotoxicity of KFMA versus FMA using Microculture tetrazolium assay of P388 cell line.

KFMA shows equal or better in vitro cytotoxic activity as compared to that of FMA, the effective concentration range being about 0.1 to 10 μg per ml (FIG. 5).

KFMA is active against gram positive bacteria and fungi at a concentration of 0.025 to 5 μg/ml (zone size 9.5 mm).

Upon hydrolysis of the potassium salt, FMA was obtained in almost quantitative (99%) yield. The HPLC and TLC give superimposable peaks and spots when compared with the FMA standard. Similar RT and Rf values are obtained.

Tests conducted with alkali metal salts of FMA showed that the antimicrobial and antitumor properties of these water soluble salts were equal or better than FMA.

TABLE 1

Physicochemical Properties of Potassium Salt of Fredericamycin A

| | |
|---|---|
| Nature: | Dark blue-green solid, highly hygroscopic. |
| Mol. Formula: | $(C_{30}H_{21}NO_9)^- k^+ n$; where n = 1, 2 or 3. |
| Mol. Wt. (FABMS): | 578, 616, 656 (mono, di or tripotassium salt respectively). |
| M.P: | (Kofler block, uncorrected) >350° C. (decomp.) |
| TLC* (Rf): | (Hydrolysed product) 0.53 |
| HPLC** (RT): | (Hydrolysed product) 6.50, 11.80 (15 cms, 30 cms column respectively, 95–99% recovery of fredericamycin A). |
| Solubility: | Readily Soluble in Dimethyl sulfoxide (8 mg/1.5 ml), dimethylacetamide, dimethylformamide, pyridine and dimethylsulfoxide-water (1:1, 3.0 mg/ml). Soluble in water (1 mg/ml), dimethylsulfoxide-water (5:95, 1.5 mg/ml), dimethylsulfoxide-saline (5:95 and 10:90 1.0 mg/ml in both but in latter the solution is transparent blue), chloroform-methanol-acetic acid (87:3:3) and methanol. Sparingly soluble in ethylacetate, acetonitrile and chloroform. Insoluble in hexanes, ether, acetone, benzene and carbon tetra chloride. |
| pH ($H_2O$): | 8.9 ± 0.2 |
| Stability: | The anhydrous salt is stable at room temp. Safely heated under high vacuum up to 60° C. (4 hrs) with no decomposition. Stored at 0° C. over $SIO_2$ tightly sealed with parafilm. DMSO solutions (anhydrous) are fairly stable at room temp (4 hrs), at 0° C./dark for several days. Easily hydrolysable to fredericamycin A in presence of moisture, acid O—AcOH (Prodrug) with change in color from dark blue to dull blue. |
| Atomic absorption: | 109 μg K/1.0 mg of K-FMA; 1.8 μg Na/1.0 mg of K-FMA. |
| *Plates: | Silica gel 60-F254, Pre-coated, 5 × 20 cms × 0.25 mm, E.M. Reagents. |
| **Solvent System: | $CHCl_3$—MeOH—AcOH (87:3:3); Detection: UV light, color and MeOH—$H_2SO_4$ spray using heat. |
| Column: | $C_{18}$ μ-bondapak-CN, 3.9 × 15 and 30 cms × 10μ stainless steel (Millipore); |
| Solvent: | $CH_3CN$—$H_2O$-AcOH 940:60:1); FLow: 1.0 ml/minute; |
| Chartspeed: | 0.5 cms/minute; Detector; UV 254 nm; 0.1 AUFS. |

TABLE 2

Assignments of the ions obtained in the negative ion mode in fast atom bombardment mass spectrum of the potassium salt of fredericamycin A.

| Ions (m/z) | Assignments |
|---|---|
| 654 | $[MQ + 3K - 2H]^-$ |
| 616 | $[MQ + 2K - H]^-$ |
| 580 | $[MHQ + K]^-$ |
| 579 | $[MHQ + K - H]^-$ |
| 578 | $[MQ + K]^-$ |
| 577 | $[MQ + K - H]^-$ |
| 576 | $[MQ + K - 2H]^-$ |
| 564 | $[MHQ + Na]^-$ |
| 563 | $[MHQ + Na - H]^-$ |
| 562 | $[MQ + Na]^-$ |
| 541 | $[MHQ]^-$ ... FM Hydroquinone form |
| 540 | $[MHQ - H]^-$ |
| 539 | $[MQ]^-$ ... FM-Quinone form |
| Other major ions: | 524, 508, 480, 464, 405, 313, 292, 281, 279, 261, 249, 233, 221 and 189. |

TABLE 3

Comparison of $^1$HNMR Protons of Potassium Salt of Fredericamycin A with Fredericamycin A in DMSO-$d_6$ at 200 MHz.

| Potassium salt of FMA | Standard FMA | Assignments |
|---|---|---|
| 1.78, (3H), d (J = 6.5 Hz) | 1.81, (3H), dd (J = 6.3, 1.2 Hz) | —$CH_3$ |
| 2.16, (2H), t (J = 7.3 Hz) | 2.50, (2H), t (J = 7.5 Hz) | —$CH_2$ |
| 3.02, (2H), t (J = 7.3 Hz) | 3.20, (2H), t (J = 7.5 Hz) | —$CH_2$ |
| 3.80, (3H), S | —* | $OCH_3$ |
| 5.80, (1H), dq (J = 15.0, 6.53 Hz) | 5.95, (1H), dq (J = 15.0, 6.0 Hz) | $H_A$ |
| 6.15, (1H), cm | 6.22, (1H), cm | $H_C$ |
| 6.20, (1H), d (J = 15.0 Hz) | 6.24, (1H), d (J = 15.9 Hz) | $H_D$ |
| 6.20, (1H), S | —* | H-7 |
| 6.42, (1H), S | 6.71, (1H), S | H-4' |
| 6.42, (1H), S | 7.07, (1H), S | H-5' |
| 7.00, (1H), dd (J = 15.0, 11.2 Hz) | 7.15, (1H), dd (J = 15.9, 10.51 Hz) | $H_B$ |
| — | 11.61, (1H), S | —NH (conc. depend) |
| — | 13.15, (1H), S | —OH |

TABLE 3-continued

Comparison of $^1$HNMR Protons of Potassium Salt of Fredericamycin A with Fredericamycin A in DMSO-$d_6$ at 200 MHz.

| Potassium salt of FMA | Standard FMA | Assignments |
|---|---|---|
| | | (conc. depend) |

*These signals are observed only after addition of trace amount of trifluoroacetic acid to the DMSO-$d_6$ solution of fredericamycin A.
Note the upfield proton shift of signals (from 0.03 to 0.65 ppm) in the potassium salt of fredericamycin A.

TABLE 4

Comparison of $^1$HNMR Protons of Potassium Salt of Fredericamycin A with Fredericamycin A in DMSO-$d_6$ + TFA-d at 200 MHz.

| KFMA | Standard FMA | Assignments |
|---|---|---|
| 1.81, (3H), dd (J = 6.22, 1.2 Hz)) | 1.81, (3H), dd (J = 6.3, 1.2 Hz) | —CH$_3$ |
| 2.50, (2H), t (J = 7.5 Hz) | 2.50, (2H), t (J = 7.5 Hz) | —CH$_2$ |
| 3.20, (2H), 5 (J = 7.5 Hz) | 3.20, (2H), t (J = 7.5 Hz) | —CH$_2$ |
| 3.98, (3H), S | 3.93, (3H), S | —OCH$_3$* |
| 5.96, (1H), dq (J = 15.9, 6.2 Hz) | 5.95, (1H), dq (J = 15.9, 6.0 Hz) | H$_A$ |
| 6.20, (1H), ddq (J = 16.0, 11.0, 1.2 Hz) | 6.22, (1H), ddq (J = 15.9, 11.0, 1.2 Hz) | H$_C$ |
| 6.24, (1H), d (J = 16.0 Hz) | 6.24, (1H), d (J = 15.9 Hz) | H$_D$ |
| 6.59, (1H), S | 6.59, (1H), S | H$_7$* |
| 6.71, (1H), bs | 6.71, (1H), bs | H-4' |
| 7.03, (1H), S | 7.07, (1H), S | H-5' |
| 7.16, (1H), dd (J = 15.9, 11.0 Hz) | 7.15, (1H), dd (J = 15.9, 10.5 Hz) | H$_B$ |
| 11.59, (1H), bs | 11.59, (1H), bs | —NH |
| | | (conc. depend) |
| 12.22, (1H), bs | 12.19, (1H), bs | 9'-OH |
| | | (conc. depend) |
| 13.14, (2H), S | 13.09 | 4-OH |
| | (2H), S | (conc. depend) |
| | 13.10 | 9-OH |
| | | (conc. depend) |

*These protons are not seen in FMA std. in DMSO-$d_6$ alone.

TABLE 5

Comparison of Ultraviolet-Visible spectra of Potassium salt of fredericamycin A and fredericamycin A (Dimethyl formamide - methanol 2:8)

| Potassium salt of FMA *C = 0.02136 g/liter *pH = 9.06 | | Fredericamycin A *C = 0.01136 g/liter *pH = 8.0 | |
|---|---|---|---|
| Wave length | $E_{1\,cm}^{1\%}$ | Wave length | $E_{1\,cm}^{1\%}$ |
| 627 | 117.50 | — | — |
| — | — | 637 | 103 |
| — | — | 509 | 126 |
| 393 | 368.81 | 392 | 449 |
| 374 | 430.71 | 373 | 560 |
| — | — | 358 | 447 |
| 333 | 358.61 | 333 | 437 |
| 318 | 397.94 | 318 | 481 |
| 306 | 377.34 | 305 | 438 |
| 260 | 664.61 | 260 | 877 |

TABLE 6

In vivo activity of potassium salt of fredericamycin A and fredericamycin A.

| | fredericamycin A (DMSO: i.p)** | | Potassium salt of fredericamycin A (water: i.p)** | | |
|---|---|---|---|---|---|
| Tumor tested | Drug dose (mg/kg) | % T/C* | Drug dose (mg/kg) | % T/C* Expt #1 | Expt #2 |
| P388 | 0.06 | 122 | .063 | 110 | 112 |
| Lymph. | 0.12 | 146 | 0.125 | 119 | 120 |
| Leu- | 0.25 | 134 | 0.25 | 119 | 132 |
| kemia | 0.50 | 200 | 0.50 | 153 | 160 |
| | 1.00 | 160 | 1.00 | 178 | 175 |
| | >1.00 | Toxic | 2.00 | Toxic | — |

*T/C is the ratio expressed in percent of the median survival time of the treated group divided by the median survival time of the control group. NCI criteria of positive (moderate) activity in P388 Leukemia is indicated by a T/C value of 120%. A T/C value of ≧ 175% is indicative of significant activity.
**DMSO = Dimethylsulfoxide; i.p = intraperitoneal route of injection. Potassium salt of fredericamycin A was dissolved in water only.

Of course, the availability of a water soluble FMA makes it possible for the first time to prepare pharmaceutical compositions in sterilized aqueous or inert medium without organic solvents. It is noted that FMA, per se, being virtually insoluble in H$_2$O, is dissolved in organic solvents such as DMSO and DMF which are toxic and undesirable compared to H$_2$O. Any suitable pharmaceutically acceptable carrier such as physiological saline, aqueous buffered media and the like can be used for the preparation of the pharmaceutical composition and any common sterilants, additives or adjuvants such as ascorbic acid, well known in the art can be added in the preparation of the pharmaceutical compositions. Such compositions can be liquid or cream-like in consistency. The composition can be used systemically or topically and in any form (tablet, injection and the like). A suitable pharmaceutical composition can be prepared wherein K-FMA or alkali metal salt is present in the amount of about 0.1 to 10 μg per ml of the aqueous solvent.

It is understood that the examples and embodiments described herein are for illustrative purposes only and that various modifications or changes in light thereof will be suggested to persons skilled in the art and are to be included within the spirit and purview of this application and the scope of the appended claims.

I claim:

1. A compound of the following formula:

wherein at least one of $R_1$, $R_2$ and $R_3$ is an alkali metal moiety, the remaining being either an alkali metal or H.

2. The compound of claim 1 having the property of being water soluble to the concentration of at least about 0.5 to 1.00 mg/ml.

3. The compound of claim 2 wherein said alkali metal is selected from the group consisting of K, Na and Li.

4. The compound of claim 3 wherein said alkali metal is K.

5. The compound of claim 4 wherein said alkali metal is Na.

6. A pharmaceutical composition comprising an effective amount of the compound of claim 1 to inhibit growth of microorganisms or tumors and a pharmaceutically acceptable carrier.

7. A method of preparing a water soluble derivative of fredericamycin A (FMA), comprising the steps of:
    (a) preparing a solution of fredericamycin A in a deoxygenated solvent;
    (b) reacting the solution of step (a) with an aqueous solution containing alkali metal hydroxide in an amount sufficient to react with FMA to produce alkali metal salt under deoxygenated conditions at about 4° C. or less for sufficient time to form alkali metal derivative of fredericamycin A;
    (c) then recovering the alkali metal derivative of fredericamycin A through lyophilization.

8. The method of claim 7 cryopreserving alkali metal-FMA under $N_2$.

* * * * *